United States Patent
Everhart et al.

(10) Patent No.: US 6,626,961 B1
(45) Date of Patent: Sep. 30, 2003

(54) NONWOVENS MODIFIED WITH PETROLATUM

(75) Inventors: Dennis S. Everhart, Alpharetta, GA (US); Ali Yahiaoui, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/559,566

(22) Filed: Apr. 27, 2000

(51) Int. Cl.⁷ .............................. D06Q 1/02; A61F 13/15
(52) U.S. Cl. ................. 8/115.51; 604/358; 604/363; 604/378; 8/115.6
(58) Field of Search ................. 8/115.51, 115.6; 604/358, 363, 378

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,901,236 A | 8/1975 | Assarsson et al. | 128/284 |
| 4,076,663 A | 2/1978 | Masuda et al. | 260/17.4 |
| 4,286,082 A | 8/1981 | Tsubakimoto et al. | 526/240 |
| 4,340,563 A | 7/1982 | Appel et al. | 264/518 |
| 4,377,458 A | 3/1983 | Watanabe | 204/159.16 |
| 4,405,689 A | 9/1983 | Watanabe | 428/467 |
| 4,634,626 A | 1/1987 | Yamaguchi et al. | 428/312.4 |
| 4,911,907 A | 3/1990 | Shimamura et al. | 424/84 |
| 5,609,587 A | 3/1997 | Roe | 604/360 |
| 5,635,191 A | 6/1997 | Roe et al. | 424/402 |
| 5,643,588 A | 7/1997 | Roe et al. | 424/402 |
| 5,665,333 A | 9/1997 | Homola et al. | 424/54 |
| 5,712,673 A | 1/1998 | Hayashi et al. | 347/217 |
| 5,763,438 A | 6/1998 | Inokuchi et al. | 514/237.8 |
| 5,951,991 A | 9/1999 | Wagner et al. | 424/401 |
| 5,980,868 A | 11/1999 | Homola et al. | 424/54 |
| 5,989,531 A | 11/1999 | Schamper et al. | 424/65 |
| 6,001,381 A | 12/1999 | Gordon et al. | 424/402 |
| 6,018,093 A | 1/2000 | Roe et al. | 604/367 |
| 6,118,041 A | * 9/2000 | Roe et al. | 604/360 |
| 6,409,713 B1 | * 6/2002 | Osborn, III et al. | 604/385.17 |

FOREIGN PATENT DOCUMENTS

| | | |
|---|---|---|
| CA | 2019557 | 12/1990 |
| WO | 00/10500 | 3/2000 |
| WO | 00/64503 | 11/2000 |

* cited by examiner

*Primary Examiner*—Yogendra N. Gupta
*Assistant Examiner*—D G Hamlin
(74) *Attorney, Agent, or Firm*—Pauley Petersen & Erickson (57) ABSTRACT

A lotion alternative, namely a nonwoven fabric treated with an aqueous-based petrolatum-surfactant mixture, simultaneously imparts fluid handling and skin health benefits during product use. The petrolatum-surfactant mixture can be applied to the nonwoven fabric by a foaming process. The foaming process is compatible with existing commercial nonwoven production equipment and in-line high production rates.

16 Claims, 2 Drawing Sheets

NONWOVENS MODIFIED WITH PETROLATUM

FIELD OF THE INVENTION

This invention relates to nonwoven webs treated with a stable aqueous formulation containing petrolatum. The invention includes a foaming process for applying the petrolatum formulation to the nonwoven web.

BACKGROUND OF THE INVENTION

A number of products made of nonwoven fabrics, such as personal care absorbent products, interact with a user's skin. Various skin disorders are often associated with use of personal care absorbent products. Diaper rash is a prime example of a skin disorder often caused, in part, by friction between a nonwoven fabric and a user's skin. A number of preventive measures have been developed and used over the years, such as topical application of creams and lotions, in order to prevent or cure diaper rash.

Skin barrier dysfunction is often associated with the loss of material and structure in the lipid-containing domains of the skin. One area of skin care product development is lipid replenishment by the external application of lotions supplemented with specific components known to be present in-vivo. Use of barrier creams, such as those containing petrolatum or mineral oil, is also common. These barrier creams typically act by occluding the skin with a hydrophobic coating. Petrolatum-based lotions are differentiated from high-value lotions containing botanical extracts in that the latter are intended to deliver an active ingredient, ostensibly to the skin.

U.S. Pat. Nos. 5,635,191 to Roe et al., 5,609,587 to Roe, and 5,643,588 to Roe et al. disclose non-aqueous waxes, striped applications, and substrates that are non-permeable by water.

Petrolatum-based lotions effectively prevent or reduce the occurrence of a number of common skin disorders. However, such lotions must be applied directly to the skin between each use of a nonwoven personal care absorbent garment, resulting in a time-consuming, often messy ritual. There is a need or desire for a topical treatment for a nonwoven substrate that can prevent or reduce the occurrence of a number of common skin disorders associated with nonwoven personal care absorbent garments. There is also a need or desire for an efficient method of applying a topical treatment to a nonwoven substrate.

SUMMARY OF THE INVENTION

In response to the discussed difficulties and problems encountered in the prior art, a new topical treatment for nonwoven substrates has been discovered. The topical treatment is a petrolatum oil-in-water emulsion. While maintaining acceptable fluid handling performance and skin hydration for the nonwoven substrate, this surface treatment is capable of delivering petrolatum to a user's skin upon substrate/skin contact. In addition, substrate softness is improved in comparison to similar, non-treated nonwoven substrates.

The topical treatment can be delivered to the nonwoven substrate by a number of various methods, including foaming, spraying, saturation dipping and high solids centrifugal application. The foaming method is accomplished by supplying petrolatum, water, air, and, optionally, an alkylated glycoside or other foaming aid to a mixing chamber, generating foam in the mixing chamber, and applying the foam to the nonwoven substrate via nozzle applicators. This method is compatible with existing commercial nonwoven production equipment.

The petrolatum emulsion is stable and possesses desirable Theological properties for in-process and in-use applications. Water insoluble additives, such as oils of botanical extracts, can be easily incorporated into the dispersion without negative effects. These oils can be delivered to the user's skin upon substrate/skin contact, along with the petrolatum. The treated nonwoven substrate can be used as a liner in various personal care garments, including diapers, wet wipes, training pants, feminine hygiene articles, and incontinence articles.

With the foregoing in mind, it is a feature and advantage of the invention to provide a surface modified nonwoven fabric capable of delivering petrolatum to skin upon material/skin contact.

It is also a feature and advantage of the invention to provide an efficient process for applying a petrolatum emulsion to a nonwoven substrate using existing commercial nonwoven production equipment.

DEFINITIONS

Within the context of this specification, each term or phrase below will include the following meaning or meanings.

"Hydrophilic" or "wettable" describes fibers or the surfaces of fibers which are wetted by the aqueous liquids in contact with the fibers. The fibers or the surfaces of the fibers may have been treated with a surfactant, a surfactant combination, or other finishing agents. The degree of wetting of the materials can, in turn, be described in terms of the geometry of the fibrous assembly, the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Layer" when used in the singular can have the dual meaning of a single element or a plurality of elements.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven fabric or web" refer to material and webs of material which are formed without the aid of a textile weaving or knitting process. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

"Personal care product" or "personal care absorbent product" refers to diapers, training pants, swim wear, absorbent underpants, baby wipes, adult incontinence products, and feminine hygiene products.

"Petrolatum" refers to a purified mixture of semisolid hydrocarbons, chiefly of the methane series of the general formula $C_nH_{2n+2}$. Yellowish to light amber or white in appearance, the semisolid, unctuous mass is practically odorless and tasteless. White petrolatum is transparent in thin layers even at 0°. Petrolatum is practically insoluble in water, glycerol, and alcohol, but is soluble in benzene, chloroform, ether, petroleum ether, carbon disulfide, and oils.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Pulp fibers" refer to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Thermoplastic" describes a polymeric material that softens when exposed to heat and which substantially returns to a nonsoftened condition when cooled to room temperature.

These terms may be defined with additional language in the remaining portions of the specification.

DETAILED DESCRIPTION OF THE PRESENTLY PREFERRED EMBODIMENTS

Stable oil-in-water dispersions of petrolatum can be formulated with non-ionic surfactants for use in the surface modification of nonwoven materials, preferably polyolefin nonwovens. These surface modified materials can be used to construct personal care absorbent products which contact a user's skin, thereby transferring therapeutic amounts of petrolatum from the material to the user's skin. The mixture of surfactants used to stabilize the oil dispersion against coalescence and phase separation maintains a hydrophilic surface on the treated nonwoven, allowing the treated material to function as a fluid transfer layer. The hydrophobic petrolatum in the coating does not alter the water wetting or fluid handling characteristics of the nonwoven which is stable to multiple water insults. Furthermore, the hydrophobic petrolatum ingredient in the coating imparts a soft and lubricious feel to the nonwoven.

The oil-in-water dispersion includes petrolatum and a surfactant mixture including a first emulsifier, such as a long chain fatty alcohol; a second emulsifier, such as an ethoxylated fatty acid ester of a sugar; and a wetting agent, including a monofatty acid ester of a sugar, for example. The dispersion is stable over a broad range of concentrations and temperatures. Stable lotion dispersions can be produced containing as high as 75 wt % petrolatum (excluding water). More particularly, the range of petrolatum concentration is in a range of 20 to 70 wt %, and even more particularly, the petrolatum concentration is in a range of 40 to 60 wt %. Lotion dispersions maintain their stability, without aggregation into large dispersed phases which settle due to density differences, in a range of temperatures of about 25° Celsius to about 60° Celsius.

The concentration of the first emulsifier is in a range of about 2 to 30 wt %, more particularly in a range of about 4 to 25 wt %, and even more particularly in a range of about 5 to 20 wt %. The concentration of the second emulsifier is in a range of about 0.1 to 20 wt %, more particularly in a range of about 0.2 to 15 wt %, and even more particularly in a range of about 0.3 to 10 wt %. The concentration of the wetting agent is in a range of about 10 to 30 wt %, more particularly in a range of about 12 to 28 wt %, and even more particularly in a range of about 15 to 25 wt %. The dispersion can contain between about 1 wt % and about 40 wt % solids. The term "solids" refers to any non-aqueous and/or particulate matter, including oils and particulate matter.

One suitable topical treatment composition includes (excluding water): 55 wt % petrolatum, 15 wt % cetyl alcohol, 22 wt % ethoxylated sorbitol monooleate and 8 wt % sorbitan palmitate. To this mixture is added roughly 60 to 70 wt % water (based on the whole composition) with high shear mixing at 60° Celsius to produce a 33 wt % solids lotion which can be readily extended with water to produce emulsions containing as little as 1 wt % solids. A petrolatum coating on the fibers of the nonwoven is produced when the water is evaporated after deposition. The coating can be applied using the foaming process described below, or any suitable deposition process.

The dispersion is versatile, as it allows incorporation of a broad range of active ingredients, such as water insoluble oils, including botanical extracts such as brazil nut oil, sunflower seed oil or avocado oil, to be co-emulsified with the petrolatum dispersed phase. These other ingredients can be added at about 2 to 40 wt % of the composition (excluding water). Fabrics treated with emulsions of petrolatum/oil mixtures can transfer both ingredients to skin, providing combined and possibly synergistic benefits associated with the two ingredients. Blends of petrolatum with other oils can be prepared with the total oil composition, namely the combination of petrolatum and other oils, as high as 75 wt % of the composition, more particularly between 50 and 60 wt % (excluding water). Equal combinations of petrolatum with mineral oil or brazil nut oil, a representative botanical extract, can be produced. Other surfactant combinations are possible, resulting in a topical treatment composition (excluding water) having a hydrophilic-lipophilic balance (HLB) range between 7 and 12.

Brazil nut oil is a model botanical extract because of its relatively high content in linoleic acid, a major component making up the fatty acid complex found in epidermal lipids. The presence of this important fatty acid is known to help maintain the barrier function of skin.

Phospholipids are another type of additive that can be incorporated in the dispersion. Phospholipids represent a broad range of compounds that play a number of roles in mammalian and non-mammalian cellular systems. While phospholipids have gained widespread applications in the food industry as excellent emulsifiers, their use in personal care applications has been limited by drawbacks such as color instability, low purity, odor and formulation difficulties. Recently a new class of synthetic phospholipids has been made commercially available, which mimic structurally and functionally the natural phospholipids. A unique advantage of the synthetic phospholipids over their natural counterparts is that they are self-preserving and thus may be particularly suitable for skin care applications. These phospholipids are commercially available from Uniqema and are produced over a broad range of chemistry. A few of the model compounds suitable for use in the lotion of the present invention include: Phospholipid PLN (polysiloxy pyrrolidone linoleyl phospholipid), Phospholipid CDM (coco PG-dimonium chloride phosphate), and Phospholipid PTC (cocamidopropyl PG-dimonium chloride phosphate), all of which are available from Uniqema.

Dimethicones are yet another type of oil that can be incorporated in the. dispersion. Dimethicones are synthetic emollients based on polydimethyl siloxanes, which are widely used in cosmetic formulations. One specific dimethicone used is Surfactant DC 193 ("DC 193") made by Dow Corning. DC 193 is suitable because of its emollience, softness, leveling and wetting characteristics.

An appropriate substrate to which the dispersion of the present invention is applied is a nonwoven web including a plurality of filaments made from one or more polymers. The nonwoven web may be a spunbond web, a meltblown web, a bonded carded web, or another type of nonwoven web, and may be present in a single layer or a multilayer composite including one or more nonwoven web layers.

A wide variety of thermoplastic polymers may be used to construct the nonwoven web, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A–B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing. Polyolefins are preferred. Polyethylene and polypropylene homopolymers and copolymers are most preferred. The nonwoven webs may have a wide variety of basis weights, preferably ranging from about 10 grams per square meter (gsm) to about 120 gsm.

The petrolatum coating as formulated in this work on the nonwoven fabrics does not alter the water wetting or fluid handling characteristics of the nonwoven. Furthermore, the treated nonwoven fabric is stable to multiple aqueous insults. The treated nonwoven fabric, which transfers therapeutic amounts of petrolatum from the material to a user's skin, can be used in a wide variety of absorbent product applications including, in particular, personal care absorbent products. Personal care absorbent products include diapers, training pants, swim wear, absorbent underpants, baby wipes, adult incontinence products, feminine hygiene products, and the like, as well as other surge and intake material products. In most absorbent products, the treated nonwoven fabric is used as a liner, thereby separating the user's skin from an absorbent media. An absorbent medium may include, for instance, pulp fibers alone or in combination with a superabsorbent material. The treated nonwoven fabric can also be used in medical absorbent products, including without limitation underpads, absorbent drapes, bandages, and medical wipes.

The pulp fibers may be any high-average fiber length pulp, low-average fiber length pulp, or mixtures of the same. Preferred pulp fibers include cellulose fibers. The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as a Kajaani Model FS-100 available from Kajaani Oy Electronics in Kajaani, Finland. Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps. For example, mixtures may contain more than about 50% by weight low-average fiber length pulp and less than about 50% by weight high-average fiber length pulp.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble (materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic super-absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,633 issued Feb. 28, 1978 to Edwards et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880, available from Stockhausen, located in Greensboro, N.C. An example of a fibrous superabsorbent is OASIS® 101, available from Technical Absorbents, located in Grimsby, United Kingdom.

The viscosity of the dispersions of the present invention is similar to that of water, offering a variety of process options for applying the oils to the nonwoven fabric. Saturation dip, spray or foam coating, common unit operations for textile treatment, are exemplary processes for depositing the petrolatum.

Control of viscosity of dispersions used for surface treatment of nonwovens is important for several reasons. The dispersion must flow and must exhibit a controllable rheological profile under the conditions and constraints of the treatment application process. The dispersion must also remain stable and "thin" under the shearing influence of the treatment equipment (pumps, hoses, etc.), and yet the dispersion must spread on the liner to allow for a uniform surface coverage. Additionally, the dispersion-treated nonwoven must not negatively impact absorbency performance of the diaper. In other words, viscosity of the dispersion applied onto the nonwoven liner must remain high enough when water is flashed-off during the drying process. The high viscosity at ambient conditions in the absence of water should minimize dispersion migration from the liner to other diaper components. As applied to the liner, the dispersion viscosity should be high enough, but should also "thin" under the effects of body movements and heat during normal use of the personal care absorbent garment to allow for easy transfer of dispersion from the liner to skin. The transferred dispersion acts as a protective barrier and as a lubricant at the skin/liner interface. A lubricious interface is believed to reduce the incidence of mechanically induced damage of the skin and related skin health issues associated with barrier function.

In carrying out a foaming process, petrolatum or a petrolatum/oil mixture is blended with a surfactant mixture including a first emulsifier, such as a long chain fatty alcohol; a second emulsifier, such as an ethoxylated fatty acid ester of a sugar; and a wetting agent, including a monofatty acid ester of a sugar, for example. A foaming aid, such as an alkylated glycoside, for example Glucopon® 220 UP ("Glucopon"), can be added to the petrolatum dispersion, in a concentration between 10 and 60 wt % of the dispersion, to generate a stable foam.

Glucopon® 220 UP ("Glucopon") is an alkyl polyglycoside that is primarily used as a foaming processing aid for the dispersion. More particularly, Glucopon is a solution of 60% octylpolyglycoside and 40% water. Alkyl polyglycosides are non-ionic surfactants that are synthesized from renewable raw materials such as fatty acids and sugars. These surfactants display excellent toxicological properties for skin care applications, and are powerful surface-active agents with good wettability and good foaming properties. Alkyl polyglycosides also have a genuine synergy with conventional surfactants and act as hydrotropes, i.e. a chemical that has the property of increasing the aqueous solubility of various slightly less soluble organic chemicals. Glucopon lowers, in a concentration-dependent manner, and stabilizes the viscosity of the dispersion of the invention. The rheological profile of the dispersion in the presence of Glucopon exhibits the same shear thinning behavior as the dispersion alone.

Figure 1:
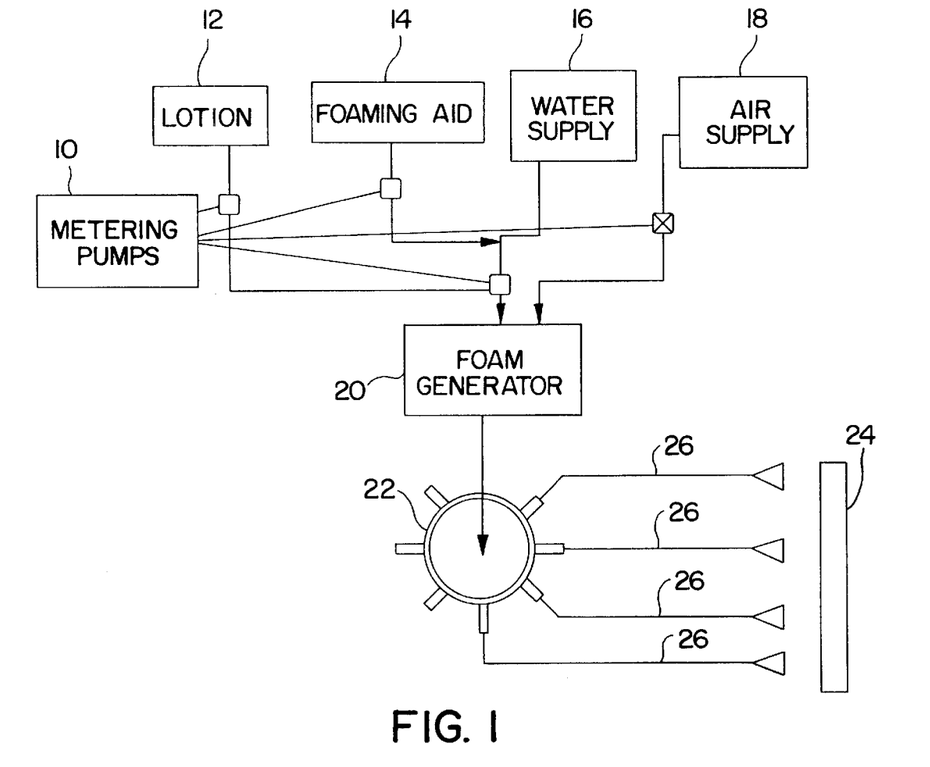
FIG. 1 is a schematic of a foam treatment application system.

This foaming process is compatible with existing commercial nonwoven production equipment. A schematic diagram of a foaming process is shown in FIG. 1. In this process, a number of metering pumps 10 are connected to a lotion supply 12 containing petrolatum and a surfactant mixture, a foaming aid supply 14, a water supply 16, and an air supply 18. The metering pumps 10 regulate the amount of lotion, foaming aid, water and air that is let into a foam generator 20. The foam generator 20 is a high-shear mixing chamber. Foam generated in the foam generator 20 is transported to a foam distributor 22 and is subsequently applied to a nonwoven liner 24 via a plurality of nozzle zone applicators 26.

The foam process offers significant advantages over the other processes in terms of equipment simplicity, ease of operation, treatment uniformity, low process variability, and cleanliness. These advantages would, therefore, make the foam process particularly useful for applications with strict requirements and tight tolerances in terms of product quality control and quality assurance, such as cosmetic products.

EXAMPLES

For the following examples, a base formulation was used to treat a commercial nonwoven liner made of Exxon PP 3155 polyolefin spunbond via a saturation dip and squeeze. The liner was produced with an average basis weight of 0.5 osy and an average fiber denier of 2.2 dpf. The composition of the base formulation, referred to as Lotion, is shown in Table 1. The commercial sources of the ingredients are also listed in Table 1.

TABLE 1

Composition of Lotion

| Ingredient | Manufacturer | Function | wt % |
|---|---|---|---|
| Petrolatum USP | Glenncorp | active | 57.1 |
| Cetyl alcohol | Aldrich | emulsifier | 14.3 |
| Span ® 40 (sorbitan monopalmitate) | Uniqema | emulsifier | 7.1 |
| Tween ® 60 (ethoxylated (20) sorbitan monostearate) | Uniqema | wetting | 21.5 |

The Lotion ingredients as shown in Table 1 were weighed and placed in a stainless steel container. The container was then placed in an oven at 60° Celsius for about 2 hours, until all ingredients were completely melted. The melted oil ingredients were then thoroughly homogenized in a high shear mixer.

Typically, a stock oil-in-water dispersion is prepared by mixing at 60° Celsius, one part of the melted and homogenized oil blended with two parts of water, thus producing a 33% solids lotion. The stock oil-in-water dispersion is also subject to high shear mixing to achieve controlled particle size and uniform dispersion of the oil particles in the continuous water phase. Final dispersions of the desired concentration and composition can be obtained by dilution of the stock oil-in-water dispersion with water and/or other active ingredients.

Average particle size and particle size distributions were determined with a Coulter N4MD particle sizer that uses an 80-channel correlator for quasi-elastic light scattering. The average particle sizes and particle size distributions determined are shown in Table 2. The base formulation was extended with 0.2 micron filtered, 18 μohm water to produce scattering counts of roughly $10^6$ counts/second. Both unimodal and size distribution profile (SDP) algorithms were used to deconvolute the autocorrelation function for particle size and distribution. Performance of the instrument was verified by measuring size standards consisting of monodispers polystyrene latex spheres of known size.

TABLE 2

Quasi Elastic Light Scattering to Determine Particle Size

| | Particle Size (microns) | |
|---|---|---|
| Wt % Solids | Unimodal | Distribution Profile |
| 0.75 | 0.715 | 0.124 (21%) |
| | | 0.830 (20%) |
| | | 4.4 (59%) |
| 1.5 | 0.813 | 0.120 (24%) |
| | | 0.760 (32%) |
| | | 7.6 (45%) |
| 5* | 0.794 | 0.172 (13%) |
| | | 1.7 (87%) |
| 15* | 1.76 | 0.130 (10%) |
| | | 4.0 (83%) |

Note:
*High shear mixer to produce this dispersion

The dispersion can be applied to a nonwoven fabric by any suitable means, including spraying, foaming and saturation dipping. In the following examples, the Lotion was applied to the nonwoven liner via a saturation dip and squeeze.

Example 1

Fluid handling of the Lotion-treated liner was evaluated using the EDANA test (Liquid Strike-Through Time 150.1-90). This test method is widely used in the nonwoven industry to measure the strike-through time, i.e. the time it takes for a known volume of liquid applied to the surface of a test piece of a nonwoven liner, which is in contact with an underlying standard absorbent blotter paper, to pass through the nonwoven. Typically, a 4"×4" liner sample is placed over 5 layers of a specified standard blotter paper whose absorbent capacity is known. The sample is placed under a circular collection reservoir, which contains a liquid sensor. Unless otherwise indicated, an insult of 5 ml saline is poured over the sample and is contained by the reservoir. The time for the insult to completely pass through the sample and absorbent papers is recorded electronically. It is believed that a fast fluid intake rate minimizes fluid pooling on the liner and thus reduces the incidence of diaper leakage. It is also believed that the faster the fluid is removed from the insult area the better it is from a skin dryness standpoint. The EDANA test can also provide information on treatment durability if the fabric is subject to multiple insults.

Figure 2:
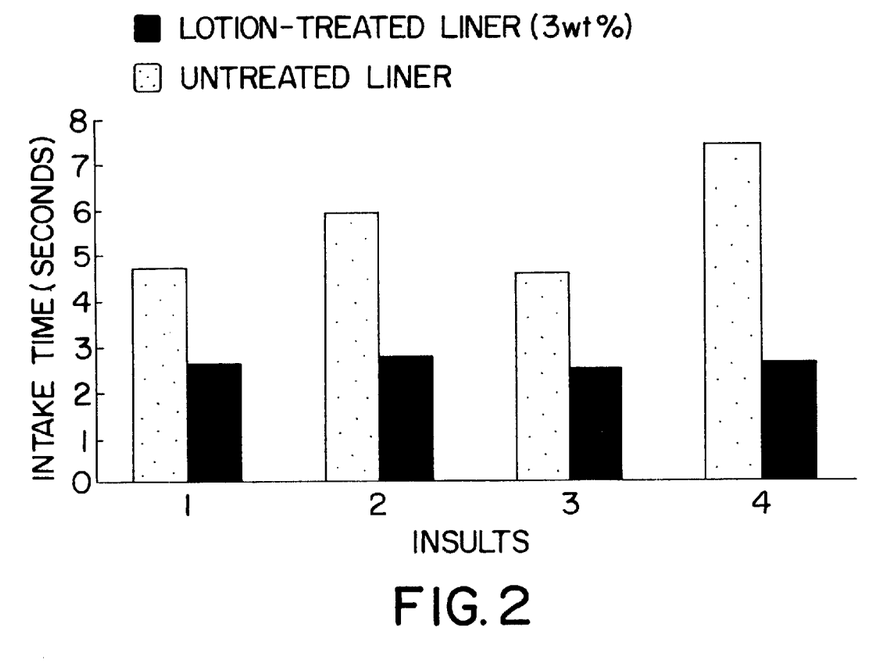
FIG. 2 is a chart showing fluid intake time for a nonwoven treated with a dispersion of the present invention compared to an untreated nonwoven.

In this example, it was important to determine if a liner treated with the Lotion containing a significant amount of petrolatum (which is hydrophobic) still can efficiently handle aqueous body fluids. The EDANA results as shown in FIG. 2, indicate that the Lotion imparts adequate intake rate to a Lotion-treated liner material. The measured intake times are significantly lower than the intake time measured on an untreated liner control. Furthermore, the Lotion treatment is durable, as the intake times remain virtually unchanged after 5 insults (FIG. 2). The fast intake time imparted by the Lotion indicates that the wetting agent (Tween 60) incorporated within the Lotion formulation is readily available on the surface of the liner. The wettability mechanism and kinetics are consistent with depression of the surface tension of the insult fluid. This mechanism is well established and usually occurs at very low surfactant levels. Although some Tween 60 leaches out of the fabric to provide wetting, most of it remains on the fabric, thus providing multiple insult performance (or durability).

Example 2

Skin dryness was tested using the Trans-Epidermal Water Loss (TEWL) test. Typically in carrying out this test, a standard diaper, in which a liner has been replaced by a test liner in all codes except the control, was mounted on the subject's inner forearm and is loaded with three standard volumes of body temperature saline at a specified flow rate. The subject wore the product for 1 hour. After this time, the product was removed and a water evaporation loss from the skin was measured over a 2-minute period. The lower the reading, the drier the product. Results shown in Table 3 were compiled as averages of 20 measurements. The results indicate that there is a statistical difference in dryness between a 3% Lotion-treated liner as compared to the current wettable liner used in the control. Table 3 also shows that no statistical difference in TEWL values for the Lotion applied at add-on levels ranging from 0.75% to 3%. Then, the TEWL test suggests that fluid transfer from the insult area to other absorbent components of the diaper is efficient, and that the potential for fluid flowback during diaper use is minimum. As the liner wettability is generally believed critical to move the fluid as quickly as it is delivered during an insult, it is also believed that excess wettability may induce undesirable excess moisture retention at the liner/ skin interface, yielding high TEWL values and undesirable skin hydration conditions.

The combined fluid intake data (FIG. 2) and TEWL data (Table 3) clearly suggest that the Lotion promotes simultaneously good fluid handling performance (i.e. primary function of a diaper) and good skin dryness conditions.

TABLE 3

Skin Dryness as Measured by TEWL

| Code | Add-on (wt %) | TEWL g/(m² hr) | Standard Deviation |
|---|---|---|---|
| Control* | NA | 38.82 | 9.80 |
| Lotion** | 0.75 | 39.09 | 7.21 |
| Lotion** | 1.75 | 40.78 | 10.48 |
| Lotion** | 3.0 | 37.32 | 9.08 |

Note:
*Commercial liner (Huggies ® Diaper) treated for wettability with a surfactant
**Lotion applied onto commercial liner (Huggies ® Diaper) using a saturation process Example 3

Softness is believed to be an important factor in assessing skin/materials interactions. It is well established that skin abrasion or disturbance of the skin would negatively affect TEWL, and thus skin hydration. Skin abrasion may also negatively affect other protective functions of skin towards biological, chemical and environmental attacks. Qualitative assessment, as in a finger-rub test of a liner, clearly indicated a significantly more lubricious sensation on a Lotion-treated liner as compared to an untreated liner. This lubricious sensation is indicative of a lower coefficient of friction at the skin/liner interface. The coefficient of friction was also measured using a Sintech Tensile Tester, ASTM D 1894. The results of this test are shown in Table 4.

The quantitative coefficient of friction results of Table 4 indicate a reduction in friction of Lotion-treated liner as compared to an untreated liner. The wettable commercial liner treated with surfactant also shows a noticeable reduction in friction as well. It is believed that mechanical irritation, such as friction and contact irritation, is an important factor in diaper dermatitis, especially when the skin is wet. The relatively low coefficient of friction measured with the Lotion is, therefore, an important attribute that can reduce the incidence of diaper dermatitis.

TABLE 4

Coefficient of Friction for Nonwoven Liner

| Liner Treatment | Coefficient of Friction |
|---|---|
| Untreated liner | 1.20 |
| Wettable commercial liner (Huggies ® Diaper) | 0.42 |
| Lotion-treated liner (1.5% add-on) | 0.37 |

Example 4

To improve transfer efficiency of petrolatum from liner to skin, attempts have been made to maximize the amount of petrolatum in the initial Lotion formulation. Compositions having various levels of petrolatum are shown in Table 5. Variants 1 and 2 contained 65.5 and 70.5% petrolatum. While these two codes were easily mixed and appeared stable and homogeneous under shear conditions, they had a tendency to phase separate overnight under no shear conditions. A higher temperature of about 60° Celsius seems to also enhance the phase separation process. Both Variants 1 and 2 contain Span® 40 as the emulsifier. On the other hand, Variant 3, containing 70.5% petrolatum but formulated with Span® 60 as the emulsifier, was relatively more stable than Variants 1 and 2 under the same conditions. It appears then that Span® 60 (sorbitan monostearate) is a more effective emulsifier at stabilizing oil phases than Span® 40 (sorbitan monopalmitate). Other Variants, shown in Table 5, having higher petrolatum content have also been successfully produced with Span® 80 (sorbitan monooleate), which is very similar to Span® 60, except that they differ only in the degree of unsaturation of the alkyl chain, $C_{18:1}$ vs. $C_{18}$, respectively.

TABLE 5

Various Petrolatum Content Formulations

| | | Composition, wt % | | Stability | |
|---|---|---|---|---|---|
| Code | Ingredients | Neat | 33% Aqueous | 25° C. | 60° C. |
| Lotion | Petrolatum | 57.1 | 19.03 | s | s |
| | Cetyl alcohol | 14.3 | 4.77 | | |
| | Span ® 40 | 7.1 | 2.37 | | |
| | Tween ® 60 | 21.5 | 7.17 | | |
| | Water | | 66.67 | | |
| Variant 1 | Petrolatum | 65.5 | 21.83 | s | us |
| | Cetyl alcohol | 10.1 | 3.37 | | |
| | Span ® 40 | 2.9 | 0.97 | | |
| | Tween ® 60 | 21.5 | 7.17 | | |
| | Water | | 66.67 | | |
| Variant 2 | Petrolatum | 70.5 | 23.5 | us | us |
| | Cetyl alcohol | 7.6 | 2.53 | | |
| | Span ® 40 | 0.4 | 0.13 | | |
| | Tween ® 60 | 21.5 | 7.17 | | |
| | Water | | 66.67 | | |
| Variant 3 | Petrolatum | 70.5 | 23.5 | s | s |
| | Cetyl alcohol | 7.6 | 2.53 | | |
| | Span ® 60 | 0.4 | 0.13 | | |
| | Tween ® 60 | 21.5 | 7.17 | | |
| | Water | | 66.67 | | |
| Variant 4 | Petrolatum | 57.1 | 19.03 | s | s |
| | Cetyl alcohol | 14.3 | 4.77 | | |
| | Span ® 80 | 7.1 | 2.37 | | |
| | Tween ® 60 | 21.5 | 7.17 | | |
| | Water | | 66.67 | | |
| Variant 5 | Petrolatum | 65.5 | 21.83 | s | s |
| | Cetyl alcohol | 10.1 | 3.37 | | |
| | Span ® 60 | 2.9 | 0.97 | | |
| | Tween ® 60 | 21.5 | 7.17 | | |
| | Water | | 66.67 | | |
| Variant 6 | Petrolatum | 65.5 | 21.83 | s | s |
| | Cetyl alcohol | 10.1 | 3.37 | | |
| | Span ® 80 | 2.9 | 0.97 | | |
| | Tween ® 60 | 21.5 | 7.17 | | |
| | Water | | 66.67 | | |
| Variant 7 | Petrolatum | 70.5 | 23.5 | s | s |
| | Cetyl alcohol | 7.6 | 2.53 | | |
| | Span ® 80 | 0.4 | 0.13 | | |
| | Tween ® 60 | 21.5 | 7.17 | | |
| | Water | | 66.67 | | |

Note:
* "s" indicates stable
** "us" indicates unstable or phase separation

While the embodiments disclosed herein are presently preferred, various modifications and improvements can be made without departing from the spirit and scope of the invention. The scope of the invention is indicated by the appended claims, and all changes that fall within the meaning and range of equivalents are intended to be embraced therein.

We claim:
1. A surface-modified nonwoven fabric, comprising:
    a nonwoven web treated with an aqueous-based dispersion of a petrolatum-surfactant mixture;

the aqueous-based dispersion including between about 60 wt % and about 99 wt % water;

the petrolatum surfactant mixture including petrolatum, a long chain fatty alcohol, an ethoxylated fatty acid ester of a sugar, and a monofatty acid ester of a sugar.

2. The nonwoven fabric of claim 1, wherein the petrolatum surfactant mixture comprises up to about 75 wt % petrolatum.

3. The nonwoven fabric of claim 1, wherein the petrolatum surfactant mixture comprises between about 20 wt % and about 70 wt % petrolatum.

4. The nonwoven fabric of claim 1, wherein the petrolatum surfactant mixture comprises between about 40 wt % and about 60 wt % petrolatum.

5. The nonwoven fabric of claim 1, wherein the petrolatum surfactant mixture comprises between about 5 wt % and about 20 wt % long chain fatty alcohol.

6. The nonwoven fabric of claim 1, wherein the petrolatum surfactant mixture comprises between about 0.1 wt % and about 20 wt % ethoxylated fatty acid ester of a sugar.

7. The nonwoven fabric of claim 1, wherein the petrolatum surfactant mixture comprises between about 10 wt % and about 30 wt % monofatty acid ester of a sugar.

8. The nonwoven fabric of claim 1, wherein the long chain fatty alcohol comprises cetyl alcohol.

9. The nonwoven fabric of claim 1, wherein the ethoxylated fatty acid ester of a sugar comprises ethoxylated sorbitol monooleate.

10. The nonwoven fabric of claim 1, wherein the monofatty acid ester of a sugar comprises sorbitan palmitate.

11. The nonwoven fabric of claim wherein the petrolatum-surfactant mixture has a hydrophilic-lipophilic balance between 7 and 12.

12. An absorbent garment comprising the nonwoven fabric of claim 1.

13. A diaper comprising the nonwoven fabric of claim 1.

14. A training pant comprising the nonwoven fabric of claim 1.

15. A feminine hygiene article comprising the nonwoven fabric of claim 1.

16. An absorbent underpant comprising the nonwoven fabric of claim 1.

* * * * *

UNITED STATES PATENT AND TRADEMARK OFFICE
CERTIFICATE OF CORRECTION

PATENT NO.     : 6,626,961 B1  
DATED          : September 30, 2003  
INVENTOR(S)    : Everhart et al.

It is certified that error appears in the above-identified patent and that said Letters Patent is hereby corrected as shown below:

<u>Column 14,</u>  
Line 9, insert -- The nonwoven fabric of claim 1, wherein the petrolatum- --

Signed and Sealed this

Twentieth Day of January, 2004

JON W. DUDAS  
*Acting Director of the United States Patent and Trademark Office*